(12) United States Patent
Duggan

(10) Patent No.: US 8,729,020 B2
(45) Date of Patent: May 20, 2014

(54) METHODS FOR THE TREATMENT OF AORTIC FIBROSIS WITH VIP FRAGMENTS

(75) Inventor: Karen Annette Duggan, Randwick (AU)

(73) Assignee: Vectus Biosystems Pty Ltd, Rosebery, NSW (AU)

(*) Notice: Subject to any disclaimer, the term of this patent is extended or adjusted under 35 U.S.C. 154(b) by 0 days.

(21) Appl. No.: 13/262,064

(22) PCT Filed: Apr. 6, 2010

(86) PCT No.: PCT/AU2010/000391
§ 371 (c)(1),
(2), (4) Date: Sep. 29, 2011

(87) PCT Pub. No.: WO2010/111753
PCT Pub. Date: Oct. 7, 2010

(65) Prior Publication Data
US 2012/0027850 A1    Feb. 2, 2012

(30) Foreign Application Priority Data
Apr. 2, 2009 (AU) ............. 2009901425

(51) Int. Cl.
*A61K 38/22* (2006.01)

(52) U.S. Cl.
USPC ............ 514/13.1; 514/17.2; 930/170

(58) Field of Classification Search
None
See application file for complete search history.

(56) References Cited

FOREIGN PATENT DOCUMENTS

| WO | 02/43746 | 6/2002 |
|---|---|---|
| WO | 2005/120545 | 12/2005 |
| WO | 2007/065226 | 6/2007 |
| WO | 2010/042997 | 4/2010 |

OTHER PUBLICATIONS

International Search Report for PCT/AU2010/000391, dated May 28, 2010.

*Primary Examiner* — Zachary Howard
(74) *Attorney, Agent, or Firm* — Roylance, Abrams, Berdo & Goodman, L.L.P.

(57) ABSTRACT

The invention relates to compositions comprising vasoactive intestinal peptide (VIP) or fragments thereof, and the use of such compositions in the treatment of aortic fibrosis and other associated conditions.

7 Claims, 4 Drawing Sheets

SEQUENCE LISTING

```
<160> NUMBER OF SEQ ID NOS: 16

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 9
<212> TYPE: PRT
<213> ORGANISM: Homo sapiens

<400> SEQUENCE: 2

Ala Val Phe Thr Asp Asn Tyr Thr Arg
1               5

<210> SEQ ID NO 3
<211> LENGTH: 13
<212> TYPE: PRT
<213> ORGANISM: Homo sapiens

<400> SEQUENCE: 3

Ala Val Phe Thr Asp Asn Tyr Thr Arg Leu Arg Lys Gln
1               5                   10

<210> SEQ ID NO 4
<211> LENGTH: 7
<212> TYPE: PRT
<213> ORGANISM: Homo sapiens

<400> SEQUENCE: 4

Ala Val Phe Thr Asp Asn Tyr
1               5

<210> SEQ ID NO 5
```

```
<211> LENGTH: 17
<212> TYPE: PRT
<213> ORGANISM: Homo sapiens

<400> SEQUENCE: 5

Ala Val Phe Thr Asp Asn Tyr Thr Arg Leu Arg Lys Gln Met Ala Val
1               5                   10                  15

Lys

<210> SEQ ID NO 6
<211> LENGTH: 21
<212> TYPE: PRT
<213> ORGANISM: Homo sapiens

<400> SEQUENCE: 6

Ala Val Phe Thr Asp Asn Tyr Thr Arg Leu Arg Lys Gln Met Ala Val
1               5                   10                  15

Lys Lys Tyr Leu Asn
            20

<210> SEQ ID NO 7
<211> LENGTH: 19
<212> TYPE: PRT
<213> ORGANISM: Homo sapiens

<400> SEQUENCE: 7

Tyr Thr Arg Leu Arg Lys Gln Met Ala Val Lys Lys Tyr Leu Asn Ser
1               5                   10                  15

Ile Leu Asn

<210> SEQ ID NO 8
<211> LENGTH: 5
<212> TYPE: PRT
<213> ORGANISM: Homo sapiens

<400> SEQUENCE: 8

Gln Met Ala Val Lys
1               5

<210> SEQ ID NO 9
<211> LENGTH: 9
<212> TYPE: PRT
<213> ORGANISM: Homo sapiens

<400> SEQUENCE: 9

Gln Met Ala Val Lys Lys Tyr Leu Asn
1               5

<210> SEQ ID NO 10
<211> LENGTH: 13
<212> TYPE: PRT
<213> ORGANISM: Homo sapiens

<400> SEQUENCE: 10

Gln Met Ala Val Lys Lys Tyr Leu Asn Ser Ile Leu Asn
1               5                   10

<210> SEQ ID NO 11
<211> LENGTH: 5
<212> TYPE: PRT
<213> ORGANISM: Homo sapiens

<400> SEQUENCE: 11

Phe Thr Asp Asn Tyr
```

```
<210> SEQ ID NO 12
<211> LENGTH: 7
<212> TYPE: PRT
<213> ORGANISM: Homo sapiens

<400> SEQUENCE: 12

Phe Thr Asp Asn Tyr Thr Arg
1               5

<210> SEQ ID NO 13
<211> LENGTH: 11
<212> TYPE: PRT
<213> ORGANISM: Homo sapiens

<400> SEQUENCE: 13

Phe Thr Asp Asn Tyr Thr Arg Leu Arg Lys Gln
1               5                   10

<210> SEQ ID NO 14
<211> LENGTH: 15
<212> TYPE: PRT
<213> ORGANISM: Homo sapiens

<400> SEQUENCE: 14

Phe Thr Asp Asn Tyr Thr Arg Leu Arg Lys Gln Met Ala Val Lys
1               5                   10                  15

<210> SEQ ID NO 15
<211> LENGTH: 19
<212> TYPE: PRT
<213> ORGANISM: Homo sapiens

<400> SEQUENCE: 15

Phe Thr Asp Asn Tyr Thr Arg Leu Arg Lys Gln Met Ala Val Lys Lys
1               5                   10                  15

Tyr Leu Asn

<210> SEQ ID NO 16
<211> LENGTH: 23
<212> TYPE: PRT
<213> ORGANISM: Homo sapiens

<400> SEQUENCE: 16

Phe Thr Asp Asn Tyr Thr Arg Leu Arg Lys Gln Met Ala Val Lys Lys
1               5                   10                  15

Tyr Leu Asn Ser Ile Leu Asn
            20
```

METHODS FOR THE TREATMENT OF AORTIC FIBROSIS WITH VIP FRAGMENTS

TECHNICAL FIELD

This invention relates to compositions and methods for therapeutic or prophylactic treatment of aortic fibrosis. In particular this invention concerns compositions comprising VIP or certain active fragments of VIP and their use in the treatment of aortic fibrosis.

BACKGROUND

Any discussion of the prior art throughout the specification should in no way be considered as an admission that such prior art is widely known or forms part of common general knowledge in the field.

The incidence of conditions such as stroke and dementia are more closely related to the level of systolic blood pressure than diastolic blood pressure. Elevations in systolic blood pressure have been thought to occur as a consequence of decreased production of the intrinsic vasodilator endothelial derived relaxing factor (EDRF) or nitric oxide (NO) resulting in increased vascular tone or vasoconstriction. This explains increases in systolic blood pressure but does not explain the falling diastolic blood pressure and the widened pulse pressure that are associated with increased cardiovascular risk. Only structural changes in the major blood vessel, the aorta, which reduce compliance and thus reduce the ability of the aorta to relax and absorb the systolic pressure wave as well as to undergo elastic recoil during cardiac filling or diastole can explain this phenomenon. Loss of elastic fibres and their replacement by collagen as well as disruption of the smooth muscle fibres by increased amounts of collagen and fibrous tissue result in a decrease in elasticity and compliance. These changes in the aortic wall cause rigidity which in turn results in a reflectance wave in response to the pressure wave of cardiac systole. The effect of the reflectance wave is to augment and further increase systolic blood pressure. The increased rigidity also prevents elastic recoil during cardiac filling, attenuates the capacity of the vasculature to maintain blood pressure in diastole, and results in a lower diastolic pressure. The difference between systolic and diastolic pressures is termed the pulse pressure. A widened pulse pressure (>90 mmHg) denotes high absolute risk for cardiovascular events such as stroke.

Currently available blood pressure lowering agents address the increased vasoconstrictor component of systolic pressure and lower both systolic and diastolic pressures by similar amounts. The failure of these agents to effect structural remodelling in the aorta means, that in patients with a widened pulse pressure, treatment is limited by diastolic pressure reductions. As a consequence, systolic blood pressure often remains above recommended target levels. Thus pulse pressure remains widened despite treatment or may be exacerbated by it and such patients remain at high risk for cardiovascular events such as stroke.

There is thus a need for therapeutic agents which will prevent and/or reverse the structural changes to the aorta.

It is an object of the present invention to overcome or ameliorate at least one of the disadvantages of the prior art, or to provide a useful alternative.

SUMMARY OF THE INVENTION

The present invention is concerned with VIP and/or VIP fragments and their use in the treatment of aortic fibrosis. The compositions of the present invention have the ability to prevent the development, or reverse established fibrosis in the aorta and thus can be used for therapeutic as well as prophylactic treatment.

According to a first aspect, the invention provides a composition for the prophylactic or therapeutic treatment of aortic fibrosis, the composition comprising a pharmaceutically effective amount of vasoactive intestinal peptide (VIP) (SEQ ID No. 1) or one or more functional VIP fragments selected from SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No.12, SEQ ID No. 13, SEQ ID No. 14, SEQ ID No. 15, or SEQ ID No. 16.

Preferably, compositions according to the present invention are administered in conjunction with a pharmaceutically acceptable carrier, which may be any of those known in the art or devised hereafter and suitable for the intended use. As well as carriers, the pharmaceutical composition of the invention may include other ingredients, including dyes, preservatives, buffers and anti-oxidants, for example. They may preferably be administered in conjunction with one or more other active agents useful in the treatment of aortic fibrosis or heart conditions. They may, for preference, be formulated for administration by oral, intravenous, intramuscular or subcuticular routes.

Other methods of administration such as patches, snuffs, nasal sprays and the like, will be clear to those skilled in the art.

The pharmaceutically effective amount of VIP or an active VIP fragment will vary according to the patient and/or with the severity of the condition to be treated. These variables can be ascertained by one skilled in the art by routine experimentation. An appropriate dosage range, as a starting point, can be derived from dosages administered in the animal models described herein, or with reference to PCT/AU2005/000835 and PCT/AU2006/001869. The compositions of the invention may be used to prevent or slow down progression of aortic fibrosis, as well as to reduce the degree of, or prevent establishment of fibrosis.

According to a second aspect, the invention provides a method of prophylactic or therapeutic treatment of aortic fibrosis in a subject, the method comprising administering to the subject at risk of developing aortic fibrosis, or to a subject having aortic fibrosis, a composition comprising a pharmaceutically effective amount of vasoactive intestinal peptide (VIP) (SEQ ID No. 1) or one or more functional VIP fragments selected from SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No.12, SEQ ID No. 13, SEQ ID No. 14, SEQ ID No. 15, or SEQ ID No. 16.

With respect to prophylactic treatment it will be understood that such a treatment would benefit subjects particularly who are at risk of developing aortic fibrosis. As an example of subjects in the risk category are those having associated conditions such as atherosclerosis, hypertension, chronic kidney disease, chronic vitamin D intoxication, vasculitis, diabetes, hypothyroidism, hyperlipidaemia, isolated systolic hypertension, stroke, heart failure, myocardial infarction, end stage kidney failure, and aortic aneurysm.

Preferably, the prophylactic treatment is used to prevent or slow down the development of fibrosis in a subject. The treatment may also be used to prevent or slow down progression of established aortic fibrosis, or alternatively, to reduce the degree of established fibrosis.

Preferably, the method further comprises administration of one or more other active agents useful in the treatment of aortic fibrosis.

It will be apparent to one skilled in the art that the pattern of use of the compositions of the invention may need to be altered for optimum effect. It may be necessary to take into account the nature of the disease or condition as well as its severity and any underlying risk or predisposition factors.

Preferably VIP or one or more functional VIP fragments are administered by a route selected from intravenous, intramuscular, by subcuticular injection, oral, sublingual or nasal.

Preferably VIP or one or more functional VIP fragments are administered in a dosage form selected from tablets, capsules, powders, liquid formulations, delayed or sustained release, patches, snuffs, nasal sprays and the like.

According to a third aspect, the invention provides vasoactive intestinal peptide (VIP) (SEQ ID No. 1) or one or more functional VIP fragments selected from SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No.12, SEQ ID No. 13, SEQ ID No. 14, SEQ ID No. 15, or SEQ ID No. 16, for use in the prophylactic or therapeutic treatment of aortic fibrosis.

Preferably, the use is to prevent or slow down progression of established aortic fibrosis. Alternatively, the use is to prevent or slow down the development of fibrosis in a subject or an at risk group. Also preferably, the use is to reduce the degree of established fibrosis.

Preferably, the use further comprises administration of one or more other active agents useful in the treatment of aortic fibrosis.

According to a fourth aspect, the invention provides use of vasoactive intestinal peptide (VIP) (SEQ ID No. 1) or one or more functional VIP fragments selected from SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No.12, SEQ ID No. 13, SEQ ID No. 14, SEQ ID No. 15, SEQ ID No. 16 in the manufacture of a medicament for the prophylactic or therapeutic treatment of aortic fibrosis.

The term "prophylactic" as used in the context of the present invention is intended inter alia to encompass treatments used to prevent or slow down the development of aortic fibrosis in the at risk group. High proportion of subjects that may be given prophylactic treatment may already have signs of aortic fibrosis or heart disease.

According to a fifth aspect, the invention provides a method of reducing collagen formation or enhancing collagen degradation in the aorta of a subject, the method comprising administering to the subject a composition comprising a pharmaceutically effective amount of vasoactive intestine peptide (VIP) (SEQ ID No. 1) or one or more functional VIP fragments selected from SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No.12, SEQ ID No. 13, SEQ ID No. 14, SEQ ID No. 15, or SEQ ID No. 16.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DESCRIPTION OF THE PREFERRED EMBODIMENT

Figure 1:
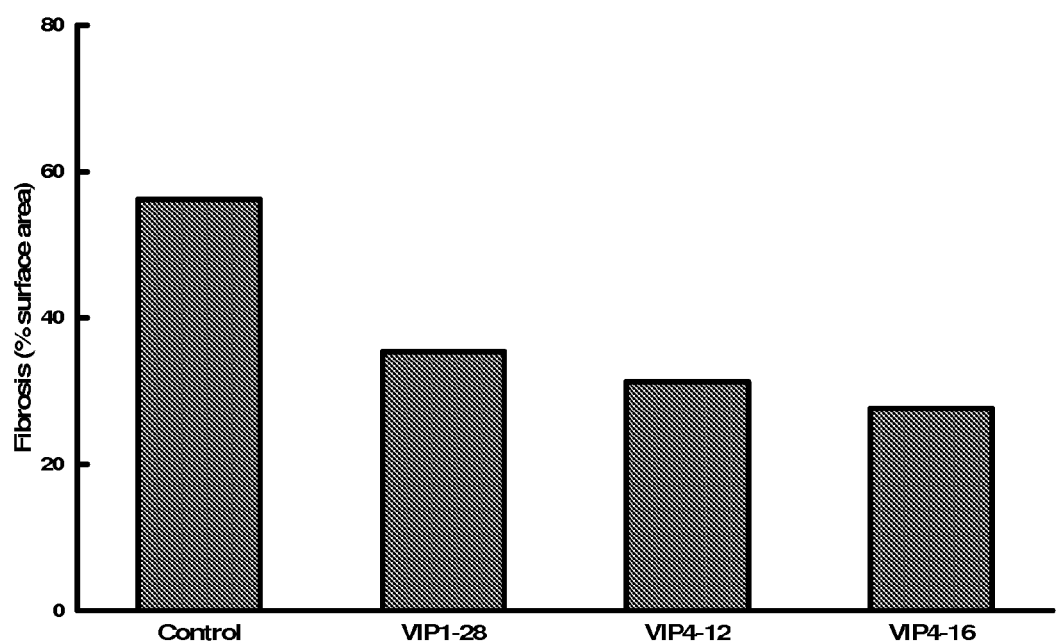
FIG. 1: Aortic fibrosis in rats after 4 weeks infusion of vehicle control or peptide at 5 pmol/kg/min.

It has now been found that the VIP molecule as a whole, acts to prevent, reduce or reverse aortic fibrosis. Further, in view of the well accepted views held in this field, it has surprisingly been found that VIP fragments lacking amino acids and motifs thought to be important for their function are nevertheless useful therapeutic agents that reverse or delay the onset of aortic fibrosis, or prevent onset of fibrosis in subjects at risk of developing heart disease. Particularly useful VIP fragments can be selected from, but not limited to, VIP (4-12), VIP (4-16), VIP (4-10), VIP (4-20), VIP (4-24), VIP (10-28), VIP (16-20), VIP (16-24), VIP (16-28), VIP (6-10), VIP (6-12), VIP (6-16), VIP (6-20), VIP (6-24), and VIP (6-28).

The use of the pharmaceutical compositions of the invention in the treatment of aortic fibrosis represents a new class of therapeutic agents for these conditions. Currently there are no existing treatments for aortic fibrosis. Without wishing to be bound by any particular mechanism of action, it is believed that the pharmaceutical preparations of the invention may target virtually all the currently known promoters of aortic fibrosis.

On the basis of the present studies, and not wishing to be bound by theory, it is postulated that VIP or VIP fragments act as major regulators to prevent the development of fibrosis, and that the depletion of VIP may unleash the synthesis of a number of profibrotic mediators, thereby causing aortic injury. The VIP fragments of the present invention seem to be able to act in much the same way as the native VIP but are more suited for therapeutic applications due to smaller size and hence increased stability and ease of manufacture.

It will be understood that the present invention also encompasses within its scope certain analogues of the VIP fragments, which are based on conservative substitutions of one or more amino acids of the VIP fragments, with amino acids which do not alter the biological activities of the VIP fragments. Such substitutions would be well known to those skilled in the art and would not require more than simple trial-and-error using well-established techniques. Hence, the term "VIP fragment" as used in the context of the present invention is intended to encompass such analogues.

All the sequences relate to VIP and fragments of human origin, but due to the very high level of amino acid conservation, VIP and fragments thereof derived from other mammalian species are also contemplated and encompassed by the present invention.

The present invention also contemplates pharmaceutical compositions, which include VIP and/or active VIP fragments. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, Remington: The Science and Practice of Pharmacy, 19$^{th}$ Edition, 1995; British Pharmacopoeia 2000, and similar formulation texts and manuals. The compositions of the present invention may also include other active agents useful in the treatment of aortic fibrosis.

The route and frequency of administration of the compositions of the present invention will depend on the treatment requirements and the nature of the molecule to be administered. Thus the formulations may be suitably prepared for administration by intravenous, intramuscular or subcuticular injection. VIP and/or VIP fragments may also be suitable for mucosal administration such as oral, sublingual, nasal and the like. These parameters are easily established by those skilled in the art.

The pharmaceutical compositions of the invention have been shown to be effective in preventing or slowing down progression of aortic fibrosis, as well as in reducing the degree (reversal) of established fibrosis and thus are important in therapeutic applications. The compositions of the present invention are therefore useful for prophylactic or therapeutic treatment of aortic fibrosis. These are important findings with respect to the range and severity of conditions, which can be treated with the compositions of the present invention.

The compositions of the present invention may be used prophylactically in subjects at risk of developing aortic fibrosis. As an example of subjects in the risk category are those having associated conditions such as atherosclerosis, hypertension, chronic kidney disease, chronic vitamin D intoxication, vasculitis, diabetes, hypothyroidism, hyperlipidaemia, isolated systolic hypertension, stroke, heart failure, myocardial infarction, end stage kidney failure, aortic aneurysm and the like.

By conserving the VIP content of the aorta in a subject with, or at risk of developing aortic fibrosis, through the use of the compositions of the present invention, significant therapeutic benefits can be achieved including reduction of fibrosis, reduction in the level, production or activity of pro-fibrotic mediators, reduction in progression of fibrosis, reduction in collagen formation or enhancing collagen degradation in the aorta.

The invention will now be described more particularly with reference to non-limiting examples.

EXPERIMENTAL

All general methodology and techniques have been described in detail in PCT/AU2005/000835, incorporated in its entirety herein by reference.

Example 1

Amino Acid Sequence of VIP and VIP Fragments

SEQ ID No 1:
VIP(1-28)-His-Ser-Asp-Ala-Val-Phe-Thr-Asp-Asn-

Tyr-Thr-Arg-Leu-Arg-Lys-Gln-Met-Ala-Val-Lys-Lys-

Tyr-Leu-Asn-Ser-Ile-Leu-Asn

SEQ ID No 2:
VIP(4-12)-Ala-Val-Phe-Thr-Asp-Asn-Tyr-Thr-Arg

SEQ ID No 3:
VIP (4-16)-Ala-Val-Phe-Thr-Asp-Asn-Tyr-Thr-Arg-

Leu-Arg-Lys-Gln

SEQ ID No 4:
VIP (4-10)-Ala-Val-Phe-Thr-Asp-Asn-Tyr

SEQ ID No 5:
VIP (4-20)-Ala-Val-Phe-Thr-Asp-Asn-Tyr-Thr-Arg-

Leu-Arg-Lys-Gln-Met-Ala-Val-Lys

SEQ ID No 6:
VIP (4-24)-Ala-Val-Phe-Thr-Asp-Asn-Tyr-Thr-Arg-

Leu-Arg-Lys-Gln-Met-Ala-Val-Lys-Lys-Tyr-Leu-Asn

SEQ ID No 7:
VIP (10-28)-Tyr-Thr-Arg-Leu-Arg-Lys-Gln-Met-Ala-

Val-Lys-Lys-Tyr-Leu-Asn-Ser-Ile-Leu-Asn

SEQ ID No 8:
VIP (16-20)-Gln-Met-Ala-Val-Lys

SEQ ID No 9:
VIP (16-24)-Gln-Met-Ala-Val-Lys-Lys-Tyr-Leu-Asn

SEQ ID No 10:
VIP (16-28)-Gln-Met-Ala-Val-Lys-Lys-Tyr-Leu-Asn-

Ser-Ile-Leu-Asn

SEQ ID No 11:
VIP (6-10)-Phe-Thr-Asp-Asn-Tyr

SEQ ID No 12:
VIP (6-12)-Phe-Thr-Asp-Asn-Tyr-Thr-Arg

SEQ ID No 13:
VIP (6-16)-Phe-Thr-Asp-Asn-Tyr-Thr-Arg-Leu-Arg-

Lys-Gln

SEQ ID No 14:
VIP (6-20)-Phe-Thr-Asp-Asn-Tyr-Thr-Arg-Leu-Arg-

Lys-Gln-Met-Ala-Val-Lys

SEQ ID No 15:
VIP (6-24)-Phe-Thr-Asp-Asn-Tyr-Thr-Arg-Leu-Arg-

Lys-Gln-Met-Ala-Val-Lys-Lys-Tyr-Leu-Asn

SEQ ID No 16:
VIP (6-28)-Phe-Thr-Asp-Asn-Tyr-Thr-Arg-Leu-Arg-

Lys-Gln-Met-Ala-Val-Lys-Lys-Tyr-Leu-Asn-Ser-Ile-

Leu-Asn

Example 2

Effect of VIP Fragment Infusion on Aortic Fibrosis in Rat Models of Fibrosis

Two animal models of aortic fibrosis were used (animals obtained from Australian Animal Resources, Perth, Western Australia, Australia)
i) Male SHR rats on 2.2% salt diet
ii) Male WKY rats on 4.4% salt diets
In each model the rats were randomised to VIP (1-28), VIP (4-12), VIP (4-16), VIP (4-10), VIP (4-20), VIP (4-24), VIP (10-28), VIP (16-20), VIP (16-24), VIP (16-28), VIP (6-10), VIP (6-12), VIP (6-16), VIP (6-20), VIP (6-24), and VIP (6-28). All peptides were obtained from or synthesised by Auspep, Australia. VIP fragments were dissolved in Hartman's solution for subsequent infusion studies.

Commencing at 12 weeks of age, the rats were acclimatized to tail cuff blood pressure measurements and handling for 2 weeks. They then underwent operative insertion of an osmotic minipump (Alzet) which was designed to deliver vehicle alone (Hartman's solution, (Baxter Health Care Corporation)-(Controls)) or VIP, VIP fragment at a dose of 5 pmol/kg/min intravenously.

The infusion was continued for 4 weeks, during which the rats were weighed and their blood pressures measured twice weekly. At the end of the 4 week infusion period, the rats were anaesthetized and their aortas harvested.

After fixation in buffered formalin, the aortas were embedded in wax, sectioned and stained with haematoxylin and eosin or with Masson Trichrome (Lomb Scientific).

For quantitation of aortic fibrosis, twenty fields from each aorta were digitized and the amount of fibrosis in each determined as percent surface area using Image-Pro Plus V5.0 software. The mean value for each rat and subsequently for each infusion group was then determined.

Figure 2:
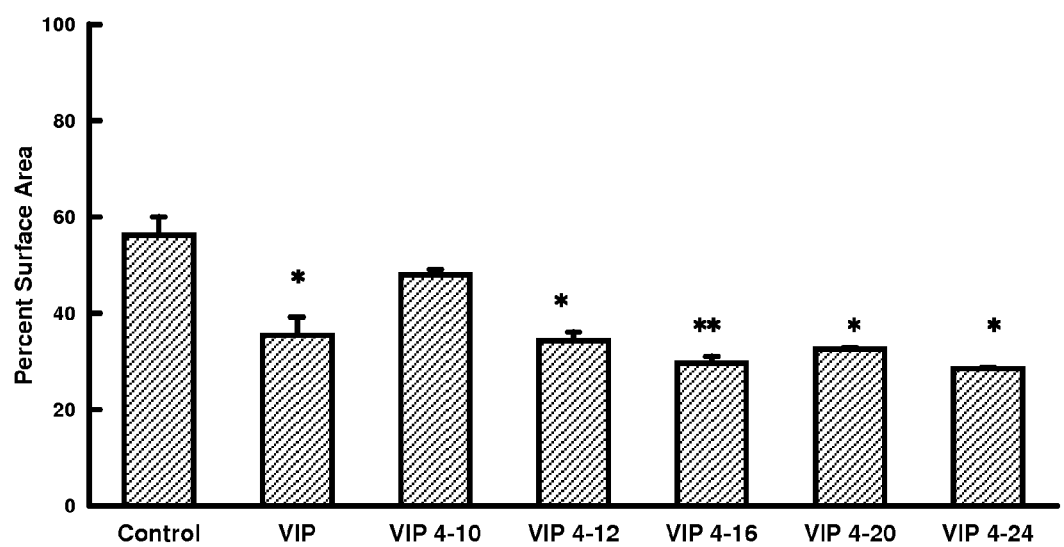
FIG. 2: Shows the effect of 4 weeks treatment with VIP and various VIP fragments at 5 pmol/kg/min in the SHR on fibrosis within the aortic wall. *$p<0.005$, **$p<0.0005$ vs Control infusion.
Figure 3:
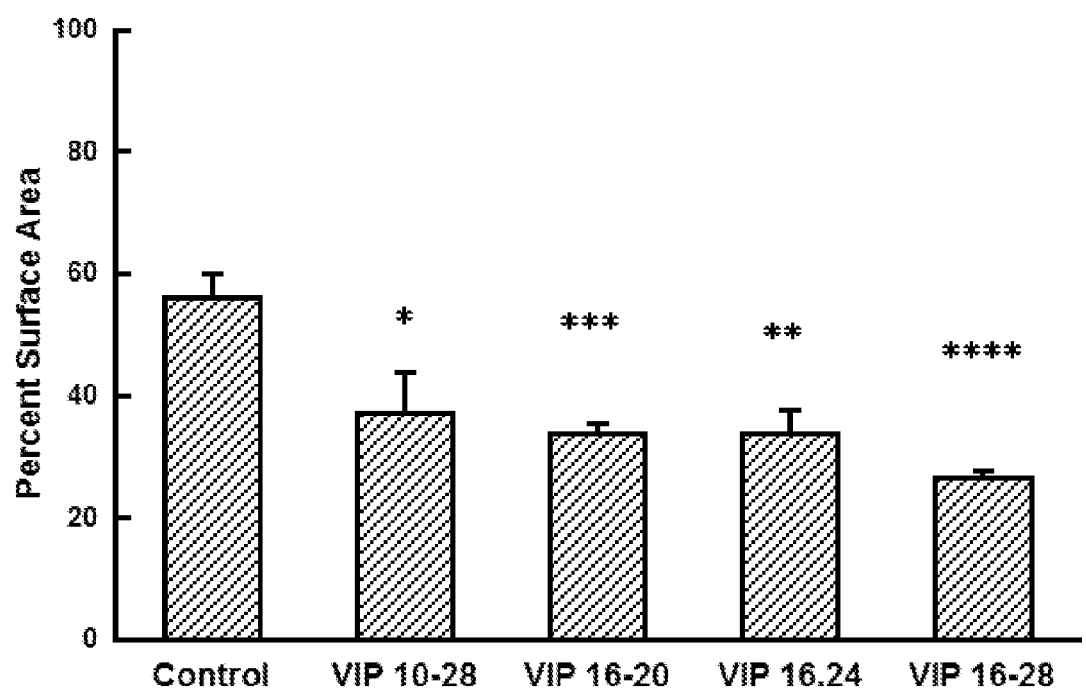
FIG. 3: Shows the effect of 4 weeks treatment with various VIP fragments at 5 pmol/kg/min in the SHR on fibrosis within the aortic wall. *$p<0.025$, $p<0.01$, *$p<0.005$ and ****$p<0.001$ vs Control infusion.
Figure 4:
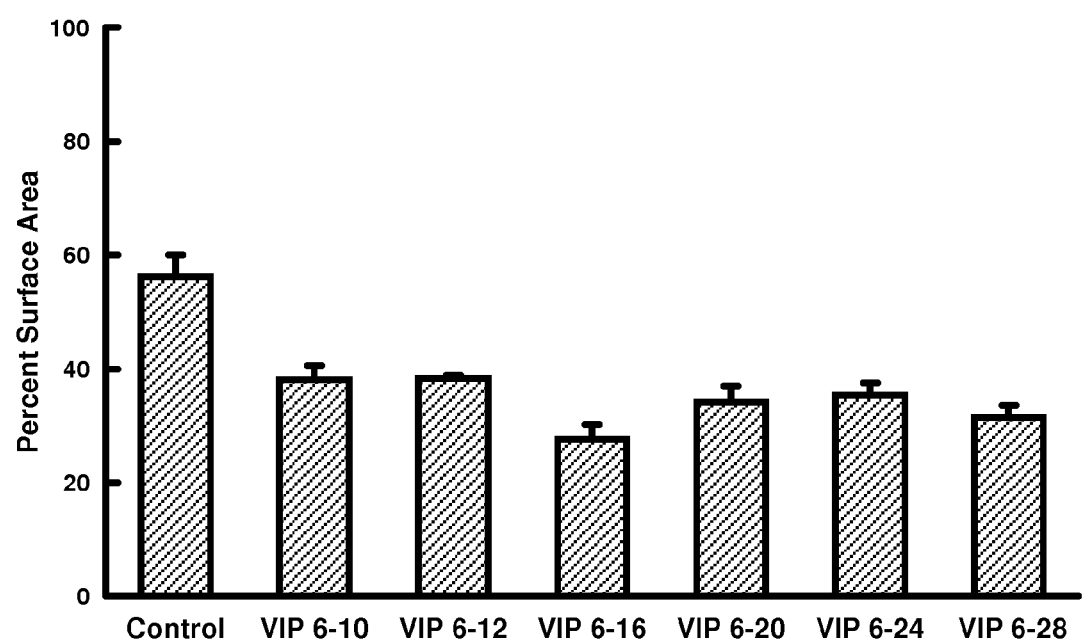
FIG. 4: Shows the effect of 4 weeks treatment with various VIP fragments at 5 pmol/kg/min in the SHR on fibrosis within the aortic wall.

FIGS. 1 to 4 show reductions in aortic fibrosis which occurred as a result of the infusion for 4 weeks of VIP and various VIP fragments in the SHR rats on a 2.2% salt diet.

The importance of the present invention to health care will be immediately apparent to one skilled in the art upon reading this disclosure. The pharmaceutical preparations of the invention, which act to prevent the progression of the underlying lesion (fibrosis), or even reverse fibrosis, have the capacity to prevent the escalation of mild to severe disease and hence to substantially reduce the health care burden. The overall size of certain VIP fragments and their activity makes them ideally suitable as targets for drug development.

It is to be appreciated that other embodiments and variants of the compositions, methods and uses of the invention, in keeping with the teaching and the spirit of the invention described, are contemplated and that these are within the scope of the invention.

---

The invention claimed is:

1. A method of therapeutic treatment of aortic fibrosis in a human subject, the method comprising administering to a human subject having aortic fibrosis a composition comprising a pharmaceutically effective amount of vasoactive intestinal peptide (VIP) (SEQ ID NO:1) or one or more functional VIP fragments selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, or SEQ ID NO:16.

2. The method according to claim 1, wherein the composition slows down the development of aortic fibrosis.

3. The method according to claim 1, wherein the composition slows down progression of aortic fibrosis, or reduces the degree of aortic fibrosis.

4. The method according to claim 1, further comprising administration of one or more other active agents useful in the treatment of aortic fibrosis.

5. The method according to claim 1, wherein the composition is administered by a route selected from intravenous, intramuscular, by subcuticular injection, oral, sublingual or nasal.

6. The method according to claim 1, wherein the composition is administered in a dosage form selected from tablets, capsules, powders, liquid formulations, delayed or sustained release, patches, snuffs, and nasal sprays.

7. The method according to claim 1, wherein the composition reduces collagen formation or enhances collagen degradation in the aorta of the human subject.

\* \* \* \* \*